United States Patent [19]

Lang et al.

[11] Patent Number: 4,465,348
[45] Date of Patent: Aug. 14, 1984

[54] APPARATUS FOR THE SUBJECTIVE AND OBJECTIVE DETERMINATION OF REFRACTION

[75] Inventors: Walter Lang; Franz Muchel, both of Königsbronn; Erich Blaha, Essingen, all of Fed. Rep. of Germany

[73] Assignee: Carl-Zeiss-Stiftung, Heidenheim/Brenz, Fed. Rep. of Germany

[21] Appl. No.: 324,403

[22] Filed: Nov. 24, 1981

[30] Foreign Application Priority Data

Nov. 29, 1980 [DE] Fed. Rep. of Germany ....... 3045139

[51] Int. Cl.$^3$ ............................ A61B 3/10; A61B 3/02
[52] U.S. Cl. ..................................... 351/211; 351/237
[58] Field of Search ............... 351/211, 237, 205, 222, 351/243

[56] References Cited

U.S. PATENT DOCUMENTS 3,874,774  4/1975  Humphrey ........................ 351/211

Primary Examiner—Rodney B. Bovernick

Attorney, Agent, or Firm—Stonebraker, Shepard & Stephens

[57] ABSTRACT

A compact apparatus for the subjective and objective determination of refraction of the eyes of a person. Two projection ray paths (6, 7), separated in space from each other, are provided, both ray paths containing systems (10, 11) for the continuous adjustment of spherical and astigmatic effects. Together with an optical telesystem (15) and the lenses of the eye they focus a test mark (3) on the retina of each of the eyes (18, 20) of the test subject. The light reflected by the retina passes via mirrors (14) into observation ray paths (21). They focus the retina and thus the test mark (3) in an image plane (30). The adjustment systems are displaced until the images of the test mark appear sharp in the image plane (30). After such an objective determination it is possible by actuating the same adjustment elements (10, 11) to adjust subjectively until the test subject sees the test mark with optimum sharpness. The projection ray paths are deflected via partially transmitting mirrors (17, 19) into the eyes of the test subject. The apparatus thus represents a free-view instrument. By inclining mirrors or the entire apparatus a near-distance vision examination is also possible.

12 Claims, 4 Drawing Figures

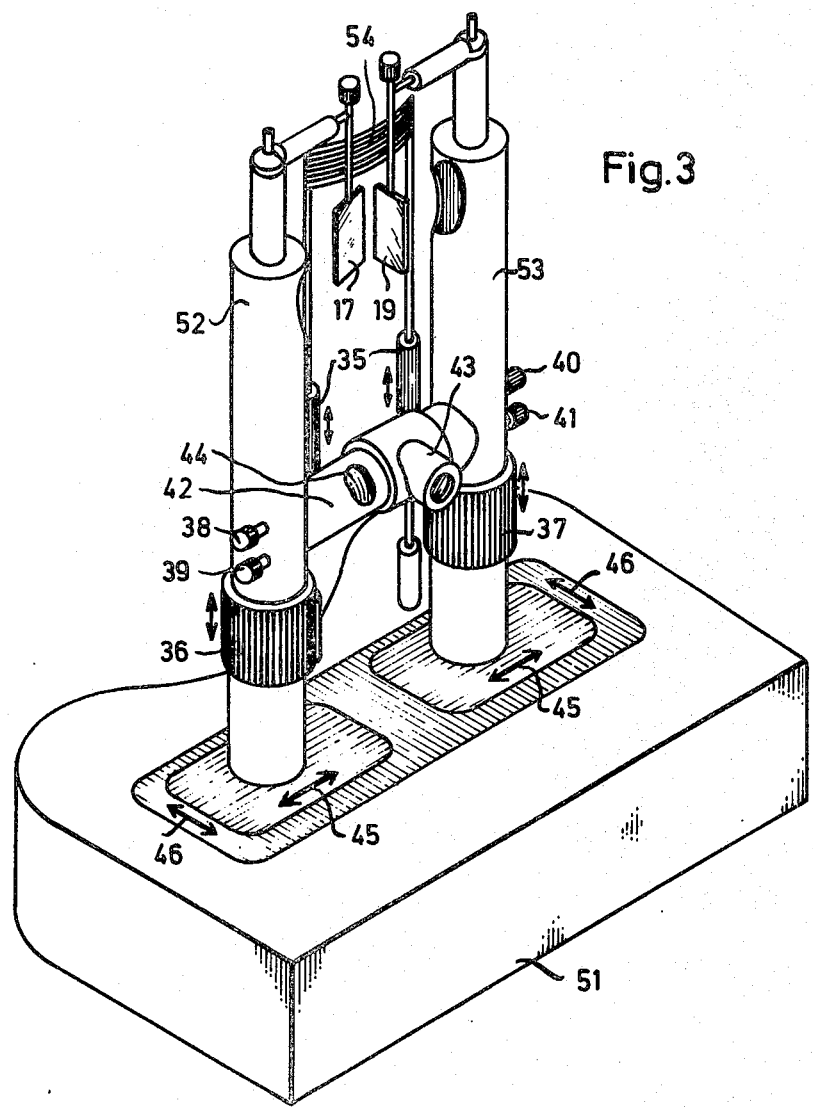

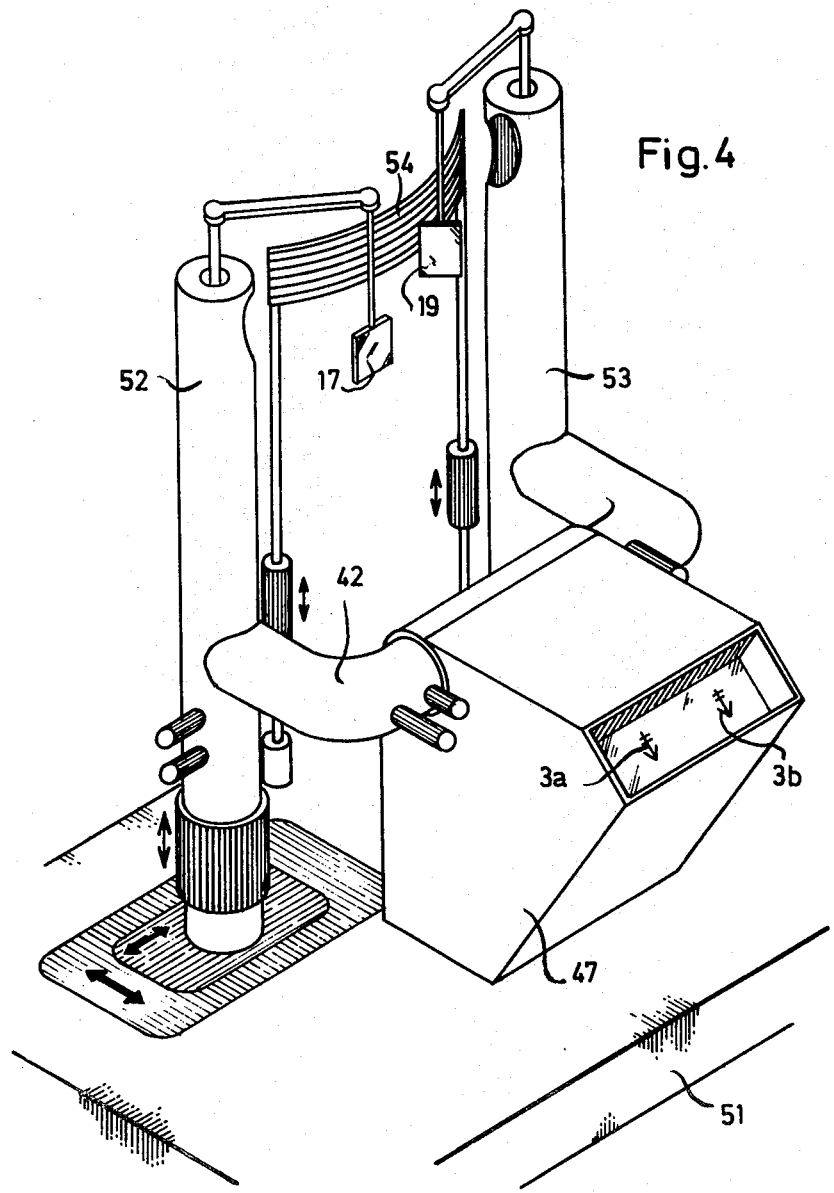

APPARATUS FOR THE SUBJECTIVE AND OBJECTIVE DETERMINATION OF REFRACTION

BACKGROUND OF THE INVENTION

The present invention relates to an apparatus for the subjective and objective determination of refraction of the human eye.

Objective-type eye refractometers are known, for instance from "ABC der Optik" (ABC of Optics) 1961, pages 742/743, in which a test object is focused on the retina of the eye to be examined and the light reflected by the eye is observed. An optical element arranged in the illumination ray path, for instance a lens or a prism, is displaced until the test image appears sharply on the retina, the position of this optical element then being a measure of the refraction value sought.

These known apparatuses have the disadvantage that they do not permit simultaneous subjective determination of the refraction, and that only a monocular determination is possible.

German Federal Republic Pat. No. 1,299,907 discloses an apparatus for the subjective and simultaneous objective determination of refraction in which two test marks are projected simultaneously in different spectral regions on a screen and the test subject observes said screen through a phoropter.

The light reflected by the retina of the eye is reflected out of the illumination ray path via a partially transmitting mirror and focused by means of an optical system in an image plane. The observer varies the setting of the phoropter until the image of the retina in said image plane is sharp. The patient can note the improvement in vision by observing one of the test marks and can thus himself participate in the optimal adjustment.

This apparatus has the disadvantage that correction is possible only in discontinuous steps and only monocularly, and that the known instrument myopia occurs, due to the phoropter which is arranged in front of the eye of the patient.

From U.S. Pat. No. 3,927,933 there is known an apparatus for the subjective and objective determination of refraction which is developed as so-called free-view apparatus. In this apparatus, a test mark is focused, via projection ray paths which are spaced from each other, onto a concave mirror which is arranged at a predetermined distance from the test subject and is viewed by the latter with both eyes. In both of the projection ray paths there are provided adjustment systems of continuously variable spherical and astigmatic action which are displaced until the test subject sees the test mark sharply. The light reflected by the eyes of the test subject is reflected-out, after reflection on the concave mirror, via a partially transmitting mirror into two observation ray paths which contain the same adjustment systems as the projection ray paths.

This apparatus has the disadvantage that the concave mirror must be relatively large so that the pupil of the eye of the test subject can adjust itself to the test image and that, as a result, the entire instrument is of very large size. Moreover, as a result of the large distance between the eyes of the test subject and the concave mirror, the displacement paths of the adjustment systems are large, and this also contributes to the large size of the instrument.

SUMMARY OF THE INVENTION

The object of the present invention is to create an apparatus, developed as a free-view instrument, for the subjective and objective determination of refraction which is particularly compact and characterized by a simple construction.

This object is achieved in accordance with the invention by arranging in front of each eye of the test subject a partially transmitting mirror for deflecting the path of a projected light ray which projects a test mark into the eye, while in front of said mirror and behind an adjustment system, as seen in the direction of the light, there is arranged a lens system whose lens facing the eye is at a distance from the pupil of the eye which is a multiple of the focal length of the lens system and which together with the eye focuses the test mark on the fundus of the eye. Also a mirror which serves for the reflecting-out of the observation ray path is arranged in the plane of the image of the pupil of the eye which is produced by the lens system.

Through the partially transmitting mirrors arranged in front of his eye the test subject sees the bright test mark superimposed on the image of the surroundings. In order to avoid the well-known instrument myopia, the apparatus itself should not be visible to the patient, i.e., the projection ray paths should advisedly extend laterally of the eyes of the test subject. This makes necessary a reflecting-in via additional mirrors and thus a relatively large back focus of the lens system serving for the focusing of the test mark. In order to be able to keep the displacement paths of the adjustment elements and thus also the size of the instrument small, this system is developed as a telesystem whose back focus is a multiple of the focal length of the system.

The relatively small instrument exit pupils in front of the eyes of the test subject require an accurate aligning of the instrument with the pupils of the eye. This is made possible by the provision of the deflection mirror, serving for the reflecting-out of the observation ray path, in the plane of the image of the pupil of the eye produced by the telesystem. By observation of this mirror and thus of the pupil of the eye the required alignment is then possible in relatively simple manner. This is particularly true if the deflection mirror is developed in such a manner that it has a central, partially transmitting region which is surrounded by a reflecting region which bears a mark.

It is advantageous to develop the test-mark projector in such a manner that it focuses the test mark at infinity. In this way a splitting up into two projection ray paths which are spaced apart from each other can take place in the parallel ray path coming from the projector, the ray paths being displaceable with respect to each other and to the projector for purposes of adjustment and the required settings.

In order to be able to make near-vision examinations also with the apparatus of the invention, the test mark projector or the test mark or the adjustment systems are so displaceable axially that the test mark appears to the test subject at a distance of, for instance, 400 mm, which corresponds to the near-vision testing distance.

Since upon near-vision testing the glance is lowered and the eyes assume a convergent position, the mirrors arranged in front of the eyes of the test subject are swingable around the center of rotation of the eye in the apparatus of the present invention. By the swinging of those mirrors in combination with the corresponding displacement of the test mark into the near-vision testing distance, the position of the eye necessary for near-vision testing is obtained. In this connection it is advantageous to couple the movements of the mirrors and the elements for the test-mark displacement so as to provide the simplest possible operation of the instrument.

It may furthermore be advantageous to mount the entire apparatus in such a manner that it can be tilted for near vision testing.

For the necessary correction of defective-vision, adjustment systems for continuous adjustment of spherical and astigmatic effects are arranged in both projection and both observation ray paths. These adjustment systems are of very simple construction and each of them consists of a spherical lens and a Stokes lens which are jointly displaceable axially.

The adjustment systems in one projection ray path and the associated observation ray path are in each case coupled for movement with each other.

The two observation ray paths are in each case so developed that the rays reflected by the eyes are focused into an image plane. This image plane is then observed by the observer via a known observation system, for instance a binocular tube. The observer can, by displacement of the adjustment systems in the ray paths under continuous observation, sharply focus the test mark on the retina of the eyes. The patient in this case observes the test mark with free and unimpeded vision and can continuously follow the objective adjustment made by the observer and also subjectively make corrections. For this purpose a subjective determination, which the test subject may also make on his own, will advisedly follow the objective determination.

Therefore, with the new apparatus it is possible to carry out for both eyes of the test subject, independently of each other, an objective and a subjective determination of refraction, with the test subject having a free unimpeded view. The apparatus itself is compact and easy to operate and permits both far-distance and near-distance examination.

BRIEF DESCRIPTION OF THE DRAWINGS

The invention will be explained in further detail below with reference to FIGS. 1 to 4 of the accompanying drawings in which:

FIG. 3 shows an embodiment in perspective, and

FIG. 4 shows another embodiment, also in perspective.

DESCRIPTION OF THE PREFERRED EMBODIMENTS

Figure 1:
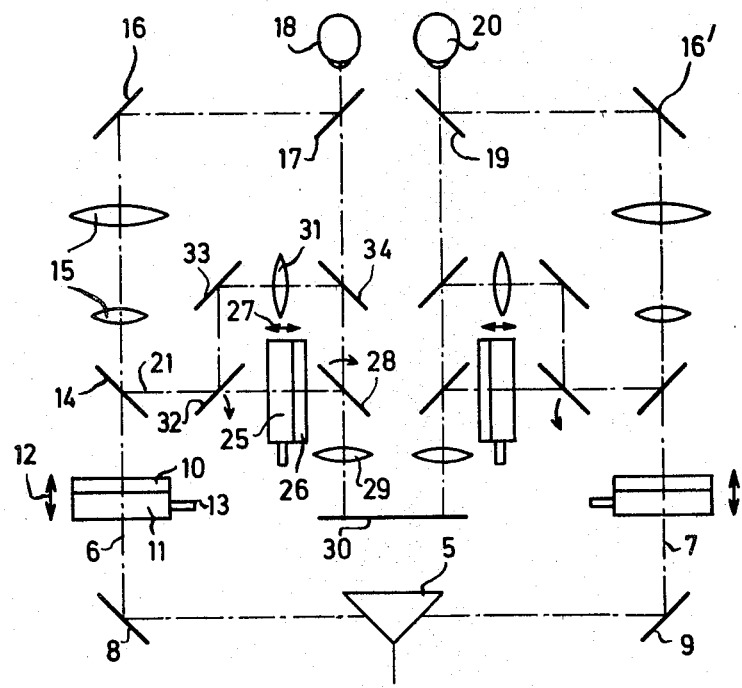
FIG. 1 shows schematically the arrangement of the optical elements in one embodiment.

In FIG. 1, 1 is a source of light which via a condenser 2, illuminates a test mark 3. A lens system indicated schematically at 4 focuses the test mark 3 at infinity. In the parallel ray path behind the lens system 4 there is a prism 5 which serves to divide the ray path into two projection ray paths 6 and 7 separated in space from each other, the mirrors 8 and 9 serving for the deflection of the rays.

The two projection ray paths 6 and 7 and associated components are symmetrical construction so that only the ray path 6 and its associated components will be explained in detail below. The corresponding components and functions are present also in the ray path 7.

The light deflected by the mirror 8 into the projection ray path 6 first of all passes through an adjustment element which consists of a spherical lens 10 and a Stokes lens 11, which lenses are axially displaceable together with each other, as indicated by the arrow 12. By means of the operating member 13 the astigmatic effect of the Stokes lens can be changed continuously. The spherical portion thereby produced can be compensated for by displacement of the adjustment system 12.

The test mark 3 is focused by the lens 10, a lens system indicated schematically at 15, and the mirrors 16, 17 onto the retina of the eye 18 to be tested. If this eye is of normal vision, then the test mark 3 is focused by the lens 10 at the projector-side focal point of the lens system 15. The eye 18 then sharply focuses the test mark 3 focused at infinity by the system 15 onto the retina, i.e. the test subject sees the test mark sharply. The mirror 17 arranged in front of the eye 18 is partially transparent so that the test subject can view the surroundings on which the bright test image is superimposed in completely relaxed manner.

For the testing of the refraction of children, they can be shown, for instance, moving images which result in a relaxation of accommodation.

If the eye 18 which is to be tested is not of normal vision, then the lens 10 is displaced axially until the test mark 3 is focused sharply on the retina of the eye. The axial position of the lens 10, i.e. the extent to which it has been displaced from a predetermined or basic position, is a measure of the spherical refraction.

Astigmatic errors in vision are corrected by actuating the Stokes lens 11. As shown, it is displaced axially together with the lens 10 since a change in distance between the lenses 10 and 11 would lead to a falsification of the astigmatic correction.

The position of the operating member 13 is a measure of the astigmatic refraction value sought.

The two projection ray paths 6 and 7 extend laterally of the eyes 18 and 20 in order to avoid instrument myopia. This results in a large distance between the mirrors 16 and 17. In order to avoid that the path of displacement for the compensation element 10, 11 and thus the size of the entire instrument becomes too large, the lens system 15 is developed as a telesystem. In this way the distance between the lens facing the eye and the pupil of the eye 18 is a multiple of the focal length of the system 15. It is, for instance, possible to impart the lens system 15 a back focus of 200 mm with a focal length of 31 mm. With such a development, a path of displacement of 1 mm of the adjustment system 10, 11 corresponds approximately to a change of one diopter of the refraction value.

The light reflected by the retina of the eye 18 is reflected-out into the observation ray path 21 by a mirror 14 arranged in the projection ray path 6. This mirror is so arranged that the lens system 15 focuses the pupil of the eye 18 into its plane.

Figure 2:
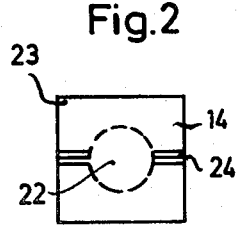
FIG. 2 shows a mirror used in the embodiment of FIG. 1 for the reflecting-out of the observation ray path, seen in top view.

The mirror 14, as shown in FIG. 2, has a central partially transmitting region 22 which is surrounded by a reflective region 23. This region 23 bears a mark 24. The projection ray path 6 passes through the central region 22. An exact adjustment of the entire apparatus is obtained when the observer sees the pupil of the eye lying in the central region 22 and the mark 24 symmetrical to it.

The mirror 14 can be swung away. In this way the exit pupil of the projection ray path can be enlarged upon the subjective examination of the eye.

The observation ray path 21 contains an adjustment system 25, 26 which has the same construction as the adjustment system 10, 11 in the projection ray path 6 and which is axially displaceable as indicated by the arrow 27. The displacement of the adjustment systems 10, 11 and 25, 26 is coupled together. The retina of the eye 18 is focused on infinity by the adjustment system 25, 26. After deflection at the swingable mirror 28, a lens system 29 produces a real image of the retina in the image plane 30.

A lens 31 is arranged parallel to the adjustment system 25, 26. By means of a swingable mirror 32 the light coming from the mirror 14 can be conducted over the mirrors 33, 34 and the lens 31. In this way an image of the pupil of the eye 18 is produced in the image plane 30.

The image plane 30 is observed by an observation system not shown here, for instance a binocular tube.

It is possible to use a source of light 1 which produces infrared light. In such case, the image produced in the plane 30 is made visible by an image converter.

The apparatus whose optical construction has been shown in FIG. 1 can be arranged in a housing such as shown in FIG. 3. The elements 1–5 are arranged in the base 51, while the tubes 52 and 53 receive the projection ray paths 6 and 7, respectively. The elements 8 and 10–16 are arranged in the tube 52; the partially transmitting mirrors 17, 19 are borne by the tubes 52, 53, respectively. 54 is a support for the head of the test subject, which can be adjusted in height by means of the rotary adjusting members 35. Two rotary rings 36, 37 on the tubes 52, 53 serve for adjusting the height of the instrument.

The actuating members 38, 40 serve for the axial displacement of the adjustment systems 10, 11 and of the adjustment systems respectively coupled with them in the observation ray path 21. The members 39, 41 serve for the adjustment of astigmatism.

The observation ray paths are arranged in the tube 42 which consists of two parts which are displaceable one within the other. On the tube 42 there is displaceably arranged a carriage 43 which can be brought optionally into the positions which make observation of the test-mark images produced in the image plane 30 possible. The test mark image produced by the left eye 18 can for instance be observed via the opening 44 in the tube 42.

The manner of operation of the instrument of FIGS. 1, 2, and 3 is as follows:

After the test subject (the person whose eyes are to be examined) has taken his place and the head support 54 as well as the instrument have been correctly adjusted in height, the interpupillary distance is set by displacing the tubes 52, 53 on the base 51 (arrows 45).

The correct determination of the condition of refraction is dependent on the corneal vertex distance. The instrument is calibrated, for instance, to a corneal vertex distance of 16 mm. First of all, focusing is effected by the lens 31 on the locus of the mirror 14 and on the mark 24. Thereupon, with the lens 31 stationary, the instrument is displaced in the direction of the arrows 46 until the pupil of the eye appears sharp, together with the mark 24, in the image plane 30. The corneal vertex distance is thus correctly set. A marking arranged symmetrically to the pupil of the instrument (not shown) is provided in the image plane 30 to permit the adjustment of the instrument laterally and vertically to the eyes of the test subject.

As next step the objective refraction is effected. For this purpose, after swinging away mirror 30 and swinging in mirror 28, the adjustment members 10 and 11 and, coupled to same, the adjustment elements 25, 26 are displaced via the actuating members 38, 39 until the test mark 3 appears sharp in the image plane. Observation is effected through the opening 44. The test subject can observe this adjustment personally and check it if light in the visible spectral region is used for the projection of the test mark 3.

After adjustment, the carriage 43 is shifted to the right and adjustment effected by actuation of the members 40, 41 until the test mark reflected by the eye 20 appears sharp in the image plane 30.

After the conclusion of the objective refraction the test subject himself or the observer can bring about an optimal correction of the defective vision by actuating the members 38, 39, 40, 41. The test subject, for this purpose, adjusts the instrument until he sees the test mark 3 with optimum sharpness with both eyes. This adjustment may be effected with continuous verification by observation of the image plane 30.

The instrument shown also makes near-vision examination possible. For this purpose, for example, the projector 1–4 is displaced axially until the test mark 3 appears in the plane of the near-vision testing distance (for instance 400 mm). At the same time, the mirrors 17, 19 are swung around the center of rotation of the eye by the angle by which the eye turns when changing direction from far distance to close distance. After the completion of this work, the required near-vision addition is determined objectively and/or subjectively in the manner described.

FIG. 4 shows an embodiment in which, instead of the observation device 43 of FIG. 3, there is used a projection attachment 47 which is connected rigidly to the base 51 and projects the test marks 3a, 3b on the image screen. Such an instrument is advantageously used when infrared light is employed for the projection of the test mark 3.

What is claimed is:

1. Apparatus for the objective and subjective determination of refraction of the eyes of a test subject, said apparatus comprising:
  (a) means forming two projection ray paths spatially separated from each other, one of said paths being associated with each eye of the test subject:
  (b) means forming two observation ray paths also spatially separated from each other and respectively associated with said two projection ray paths;
  (c) each projection ray path including a lens system (15) serving to image a test mark onto the retina of the associated eye;
  (d) each observation ray path including an optical system (29) serving to focus light reflected from the retina of the associated eye at an observation plane;
  (e) a first mirror (14) in each of said projection ray paths for reflecting light returning from the retina into the associated observation ray path;
  (f) adjustment means (10, 11; 25, 26) arranged in each of said paths for adjusting continuously both astigmatism and spherical power in said optical systems in the respective ray paths;

(g) each of said ray paths having therein a partially transmitting mirror (17, 19) arranged in front of the associated eye for reflecting light projected along a projection ray path into said associated eye and also for transmitting other light through said mirror to said associated eye so that the eye may view surrounding objects;

(h) said lens system (15) being located in each projection ray path between said partially transmitting mirror (17, 19) and said adjustment means (10, 11) in such path;

(i) the lens of said lens system (15) which is closest to the associated eye being at a distance from the pupil of the eye which is a multiple of the focal length of the lens system;

(j) said first mirror (14) being located at the plane of an image of the pupil of said eye produced by said lens system (15).

2. The invention defined in claim 1, wherein each of said partially transmitting mirrors (17, 19) is a simple flat mirror.

3. The invention defined in claim 1, further comprising a test mark projector (1–4) including means for focusing a test mark (3) optionally either at infinity or at a predetermined distance, and reflection means (5) for splitting a beam from said projector into two beams passing respectively along said two projection ray paths (6, 7).

4. The invention defined in claim 1, wherein said adjustment means (10, 11; 25, 26) for adjusting both astigmatism and spherical power includes an astigmatism adjusting element (10, 26) and a spherical power adjusting element (11, 25), the two elements being coupled to each other for joint axial movement along the ray path in which they are located.

5. The invention defined in claim 4, wherein said adjusting elements in a projection ray path are coupled to the adjusting elements in the associated observation ray path for joint axial movement therewith along their respective ray paths.

6. The invention defined in claim 1, wherein said optical system (29) is at a point in its observation ray path which is between said adjustment means (25, 26) in such path and said observation plane (30).

7. The invention defined in claim 1, further comprising a second optical system (31), and optionally usable means (28, 32, 33, 34) for directing an associated observation ray path alternatively either through said adjustment means (25, 26) associated with such path or through said second optical system (31).

8. The invention defined in claim 1, wherein said first mirror (14) has a central region (22) which is partially transmitting, surrounded by a second region (23) which is reflecting, and a reference mark (24) on said second region.

9. The invention defined in claim 1, wherein said two projection ray paths, throughout the major portions of their respective lengths, are substantially parallel to each other and are widely separated laterally from each other by a distance substantially greater than the interpupillary distance of the eyes of said test subject and are enclosed in separate laterally spaced housings, said ray paths then respectively approaching said eyes laterally and being reflected into said eyes by said partially transmitting mirrors (17, 19) so that said test subject may look through said mirrors and through the space between said housings to see other objects in the vicinity, thus promoting relaxation of the test subject.

10. Apparatus according to claim 1, wherein said partially transmitting mirrors (17, 19) arranged in front of the eyes (18, 20) of the test subject are swingable around the center of rotation of the corresponding eye.

11. Apparatus according to claim 1, further comprising a base housing (51), and two cylindrical housings (52, 53) mounted on said base housing and displaceable thereon relative to each other to adjust the interpupillary distance and the corneal vertex distance, a test-mark projector (1–4) and reflection means (5) for dividing the ray path coming from the projector being located in said base housing, and at least some elements of the projection ray paths (6, 7) being located in said cylindrical housings.

12. Apparatus according to claim 11, characterized by the fact that said base housing (51) is tiltable together with said cylindrical housings (52, 53) for near-vision examination.

* * * * *